US009322762B2

(12) United States Patent
Cercueil et al.

(10) Patent No.: US 9,322,762 B2
(45) Date of Patent: Apr. 26, 2016

(54) METHOD AND DEVICE FOR MONITORING AGEING OF ELECTRIC EQUIPMENT

(71) Applicant: SCHNEIDER ELECTRIC INDUSTRIES SAS, Rueil Malmaison (FR)

(72) Inventors: Michel Cercueil, Pont de Claix (FR); Marc Houdray, Grenoble (FR)

(73) Assignee: SCHNEIDER ELECTRIC INDUSTRIES SAS, Rueil Malmaison (FR)

( * ) Notice: Subject to any disclaimer, the term of this patent is extended or adjusted under 35 U.S.C. 154(b) by 511 days.

(21) Appl. No.: 13/783,921

(22) Filed: Mar. 4, 2013

(65) Prior Publication Data
US 2013/0231872 A1    Sep. 5, 2013

(30) Foreign Application Priority Data

Mar. 5, 2012 (FR) ...................... 12 00653

(51) Int. Cl.
*G01N 17/00* (2006.01)
*G05B 19/4065* (2006.01)

(52) U.S. Cl.
CPC ............ *G01N 17/00* (2013.01); *G05B 19/4065* (2013.01)

(58) Field of Classification Search
CPC .............................. G01N 17/00; G05B 19/4065
See application file for complete search history.

(56) References Cited

U.S. PATENT DOCUMENTS

| 6,490,543 | B1 | 12/2002 | Jaw |
| 2001/0007971 | A1 | 7/2001 | Okada |
| 2005/0143956 | A1 | 6/2005 | Long et al. |
| 2010/0082267 | A1 | 4/2010 | Schimert et al. |

FOREIGN PATENT DOCUMENTS

EP    1 117 022 A2    7/2001

OTHER PUBLICATIONS

Jouseau et al., Exhibition of an Ageing Criterion Based on Partial Discharge Detection for Medium Voltage Equipment, Sep. 7-9, 2005, SDEMPED 2005—International Symposium on Diagnostics for Electric Machines, Power Electronics and Drives, Vienna, Austria, 5 pp.*
French Preliminary Search Report issued Oct. 29, 2012, in French 1200653, filed Mar. 5, 2012 (with English Translation of Categories of Cited Documents).

* cited by examiner

*Primary Examiner* — Toan Le
(74) *Attorney, Agent, or Firm* — Oblon, McClelland, Maier & Neustadt, L.L.P.

(57) ABSTRACT

A monitoring method, device, and electric installation for monitoring ageing of at least one electric equipment unit. The monitoring method includes entering and storing ageing computation data by type of equipment, measuring physical quantities representative of environmental conditions of the electric equipment unit, the measuring of the physical quantities including measuring humidity content with a humidity sensor and measuring salinity content with a salinity sensor, computing ageing according to the measured physical quantities including the humidity content and the salinity content, and according to the stored ageing computation data, and generating electric equipment ageing data that indicates the ageing of the electric equipment unit.

14 Claims, 6 Drawing Sheets

METHOD AND DEVICE FOR MONITORING AGEING OF ELECTRIC EQUIPMENT

BACKGROUND OF THE INVENTION

The invention relates to a method for monitoring ageing of at least one electric equipment unit.

The invention relates to a device for monitoring ageing of at least one electric equipment unit comprising processing means and communication means designed to be connected to at least one electric equipment unit.

The invention also relates to an electric installation comprising monitoring of ageing of at least one electric equipment unit comprising processing means and communication means designed to be connected to said electric equipment unit.

STATE OF THE ART

It is known to perform operations involving computation of lifetime or of mean time between failures for electronic, electric or mechanical equipment. These computations are performed according to rules and tables depending on the complexity of the systems and their operating conditions. Generally, when the computations are performed, the operating conditions are stable or continuous and do not take account of unpredictable variations which may occur during the lifetime of the products.

Under these conditions, ageing is assumed to be linear and depends on the time remaining with respect to the initially computed lifetime. However, to maintain an installation correctly, it is sometimes necessary to predict ageing in a more precise and more realistic manner. Devices according to the state of the art do not enable such monitoring of ageing of electric equipment.

SUMMARY OF THE INVENTION

The object of the invention is to provide a method and a device for monitoring ageing of electric equipment enabling a more precise evaluation of the state of the equipment units to be made, as well as an installation implementing this method.

According to the invention, a method for monitoring ageing of at least one electric equipment unit comprises:
  entering and storing ageing computation data by type of equipment,
  measurement of physical quantities representative of environmental conditions,
  computation of ageing according to said measurements and to the stored ageing computation data, and
  communication and/or indication of electric equipment ageing data.

Advantageously, the monitoring method comprises functional conditions comprising:
  counting of the operations of an electric equipment unit,
  measurement of the conditions of the operations of the electric equipment unit, and
  recording of data representative of operations associated with broken current values.

Measurement of physical quantities representative of environmental conditions preferably comprises:
  temperature measurement and storage by a sensor close to said electric equipment units,
  measurement and storage of the humidity content,
  measurement and storage of the salinity content, and/or
  measurement and storage of amplitude and frequency of vibrations.

Ageing computation preferably comprises:
  computation of ageing of the mechanical part and/or of the wear of electric contacts of said equipment unit,
  computation of ageing of the electronic part of said equipment unit, and/or
  computation of ageing of an electromagnetic actuator of said electric equipment unit.

Advantageously, the monitoring method comprises determination of ageing acceleration factors.

Preferably, the monitoring method comprises selection of a maximum ageing acceleration factor from several ageing acceleration factors.

Advantageously, the monitoring method comprises modification of a value of the ageing acceleration factor due to temperature from a temperature threshold.

Advantageously, the monitoring method comprises combination of an ageing acceleration factor due to temperature with ageing acceleration factors representative of an ambient temperature, of an electric load, of harmonic current effects and/or of a tightness rating of said electric equipment unit.

According to the invention, in a device for monitoring ageing of at least one electric equipment unit comprising processing means and communication means designed to be connected to at least one electric equipment unit, the processing means comprise means for implementing a method as defined in the foregoing.

Said processing means preferably comprise:
  means for storing characteristics for computing ageing of electric equipment units,
  measurement inputs designed to be connected to measurement sensors of environmental physical quantities,
  means for indicating ageing of electric equipment units, and
  communication means.

Advantageously, the monitoring device comprises measurement sensors of environmental physical quantities connected to said processing means.

Measurement sensors of environmental physical quantities preferably comprise:
  a temperature sensor situated in a space close to said electric equipment units,
  a humidity content sensor,
  a salinity content sensor, and/or
  a vibration amplitude and frequency sensor.

In an electric installation according to the invention comprising monitoring of ageing of at least one electric equipment unit comprising processing means and communication means designed to be connected to an electric equipment unit, the processing means comprise means for implementing a method as defined in the foregoing.

Advantageously, the electric installation comprising electric equipment units comprises at least one device as defined in the foregoing connected by communication means to said electric equipment units to receive operating data.

BRIEF DESCRIPTION OF THE DRAWINGS

Other advantages and features will become more clearly apparent from the following description of particular embodiments of the invention, given for non-restrictive example purposes only, and represented in the appended diagrams in which.

DETAILED DESCRIPTION OF PREFERRED EMBODIMENTS

Figure 1:
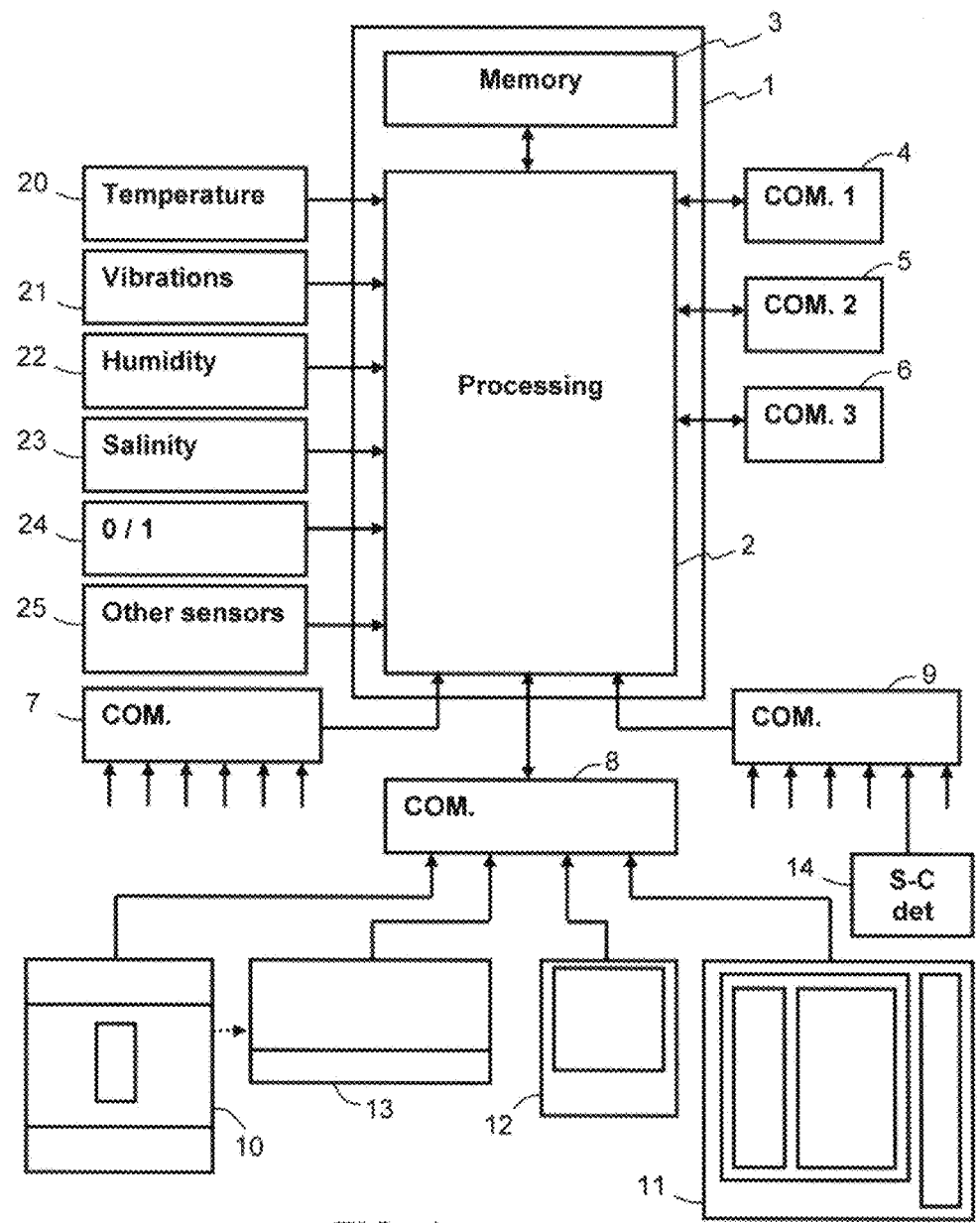
FIG. 1 represents a diagram of a device for monitoring ageing of electric equipment according to an embodiment of the invention.

In embodiments of the invention, ageing computation in particular concerns control units for electronic or thermomagnetic trip devices, the whole range of circuit breakers or contactors with power contacts and their mechanism, and actuating coils in particular undervoltage or overvoltage releases.

For example, in a circuit breaker, ageing is due in particular to environmental conditions such as temperature or vibrations, or operations performed when in service such as opening or closing operations of power contacts.

Lifetime is representative of a mean time between manufacture and a failure with given operating conditions whereas ageing concerns the percentage of life expectancy of a device or an equipment unit already elapsed for a certain time and the action of reducing this percentage.

Device lifetime is thus subject to the influence of the following factors: the number of operations with the conditions of each operation such as interrupted currents, operating temperature, presence of a corrosive atmosphere such as humidity, a salt-laden atmosphere, presence of corrosive gas (SO2, H2S, Cl2, NH3 and NON2), presence of dust, and/or presence of vibrations.

These factors can be measured by sensors, evaluated by one of the direct or indirect measurements or provided by the user via a man-machine interface, for example on the installation site.

Ageing computation is preferably performed by zones, for example by means of formula 1.

$$\% \ Ag = \% \ Ag_0 + \sum_i \frac{\Delta t_i}{(TF)_i} \qquad (1)$$
$$= \% \ Ag_0 + \frac{1}{TF_0} \cdot \sum_i \Delta t_i \cdot A_i$$

In which:
% $Ag_0$ ageing at time $t_0$,
$\Delta t$: time spent in the operating conditions zone since $t_0$,
(TF): estimated operating time before failure calculated with the operating conditions of said zone,
$TF_0$: operating time before failure under nominal conditions. This value will be defined by equipment unit reference in databases.
$A_i$: acceleration factor for the operating conditions of said zone.

The acceleration factors are local parameters enabling the initially scheduled ageing rate to be modified.

Thus, the conditions being considered to remain constant, a remaining lifetime can be computed by means of formula 2.

$$RLT = T_F \cdot (1 - \% \ Ag) \qquad (2)$$
$$= \frac{TF_0}{A_{RLT}} \cdot (1 - \% \ Ag)$$

In which:
RLT: remaining life expectancy,
$T_F$: operating time before failure computed with current operating conditions,
$A_{RLT}$: acceleration factor computed for the current operating conditions.

The ageing percentage represents a current state of the device or of the equipment unit. On the contrary, the remaining lifetime is a forecast on the state of the device or of the equipment unit, the operating conditions being considered to be constant. The remaining lifetime should therefore not be interpreted as a failure date.

For each ageing factor, the user specifies a reference period. The current acceleration factor will then be the mean instantaneous acceleration factor during an elapsed period. For computation of an ageing acceleration factor $A_{RLT}$: during an elapsed period $\tau_{RLT}$, formula 3 can be used.

$$A_{RLT}(t) = \frac{1}{\tau_{RLT}} \cdot \sum_i A_i \cdot \Delta t_i \qquad (3)$$

$\Delta t_i$ is the time spent in the operating conditions zone during the elapsed time period $\tau_{RLT}$.

When several independent ageing factors occur simultaneously, the resulting ageing is the maximum of the ageing computed for each factor.

$$\% \ Ag = \max[\% \ Ag(\text{Temperature}), \% \ Ag(\text{corrosion}), \% \ Ag(\text{operations}), \ldots] \qquad (4)$$

$$RLT = \min[T_F \cdot (1 - \% \ Ag(\text{Temperature})), T_F \cdot (1 - \% \ Ag(\text{corrosion})), \ldots] \qquad (5)$$

For an electronic device, a temperature up to 85° C. has little effect. Above this temperature, an acceleration factor is applied for computing the estimation of premature ageing. The presence of thermal cycles can also give rise to the use of additional acceleration factors.

Electronic circuits are also subject to ageing caused by corrosion resulting from three main factors such as humidity, corrosive gas (SO2, H2S, Cl2, NH3 and NON2) and salt-laden atmosphere. These three factors are not completely independent as the humidity increases the corrosive gaseous and salt-laden atmosphere effect. The following formula will for example be used:

$$A_C = 1 + (A_H - 1) + [\max(A_{CG}, A_{SA}) - 1] \qquad (6)$$

$A_C$: acceleration factor for ageing due to corrosion,
$A_H$: acceleration factor for ageing due to humidity,
$A_{GC}$: acceleration factor for ageing due to corrosive gas,
$A_{SA}$: acceleration factor for ageing due to salt-laden atmosphere.

To perform evaluation of the lifetime of a circuit breaker taking environmental ageing factors into consideration, the following formula will for example be used:

$$A = \max[\max(A_{SA}, A_{CG}) \times A_H, A_D, A_V] \times A_T \qquad (7)$$

$A_{SA}$ acceleration factor for ageing due to salt-laden atmosphere.
$A_{GC}$: acceleration factor for ageing due to corrosive gas.
$A_H$ acceleration factor for ageing due to humidity.
$A_D$: acceleration factor for ageing due to dust.
$A_V$: acceleration factor for ageing due to vibrations.
$A_T$: acceleration factor for ageing due to temperature.

The temperature acceleration factor is evaluated by a combination of the ambient temperature, the load, the harmonic effects and the tightness rating of the equipment unit. Such that:

$$A_T = A_{AT} \cdot A_{Ha} \cdot A_{IP} \cdot A_{load} \quad (8)$$

The device for monitoring ageing of electric equipment according to an embodiment of the invention represented in FIG. 1 comprises a processing module 1 represented by an enclosure 1 containing a processing circuit 2 performing computation and communication management and also data receipt and transmission. Module 1 also comprises a storage module 3 for storing electric equipment ageing characteristics and data representative of said electric equipment. The storage module 3 also stores the diagram of the electric installation with the connections of the equipment units and their type. This data can be shared, exchanged or duplicated with a supervisor or other storage modules. To communicate with other devices or a supervisor, the processing module comprises at least one hard-wired communication circuit 4, and/or a wireless communication circuit 5, and/or a communication circuit 6 via a cell phone network.

Display on a supervisor can be represented by a global or partial wiring diagram of the installation showing the states of each equipment unit as well as the references, characteristics and settings. Indication can also be performed on portable computers, tablets or mobile phones via wireless connections or via a cell phone network.

A monitoring device according to an embodiment of the invention comprises a data communication network between the electric equipment units and the processing means to communicate data. The communication network can comprise the communication concentrators 7, 8, 9 to reduce the number of communication inputs of the processing module. The concentrators are connected to several electric equipment units 10, 11, 12, 13, 14 to communicate, among other information, data on operating conditions and equipment type and references to the processing module 2 grouping the messages on a communication channel.

The electric equipment units are in particular circuit breakers 10, 11, with for example electronic trip units or protective relays. The equipment units can also be differential or earth leakage detection modules or relays 12 or power measurement modules 13, preferably associated with switchgear units such as circuit breakers or contactors. Likewise, short-circuit detectors 14 can give information on the state of an electric line or of a load to prevent closing of an equipment unit or to locate an electric short-circuit fault.

The device of FIG. 1 for monitoring ageing of electric equipment comprises measurement inputs designed to be connected to measurement sensors of environmental physical quantities. It communicates and provides indications of ageing of electric equipment in local or remote manner. Measurement sensors of environmental physical quantities are thus connected to the processing module 1.

The measurement sensors of environmental physical quantities in particular comprise:
 a temperature sensor 20 preferably situated in a space close to the electric equipment units concerned by ageing computation,
 a vibration amplitude and frequency sensor 21,
 a humidity content sensor 22, and/or
 a salinity content sensor 23.

A binary input sensor 24 can also be connected to the module 1 for ageing computation. In this case, it can for example count the number of operations of an electric equipment unit. Other sensors 25 can also be connected to the module 1 for determining an ageing rate.

The sensors 20 to 25 can be permanent sensors or sensors installed only when measurements are made. Furthermore, certain data such as the salinity or dust content can be determined previously and input directly by manual entry.

Figure 2:
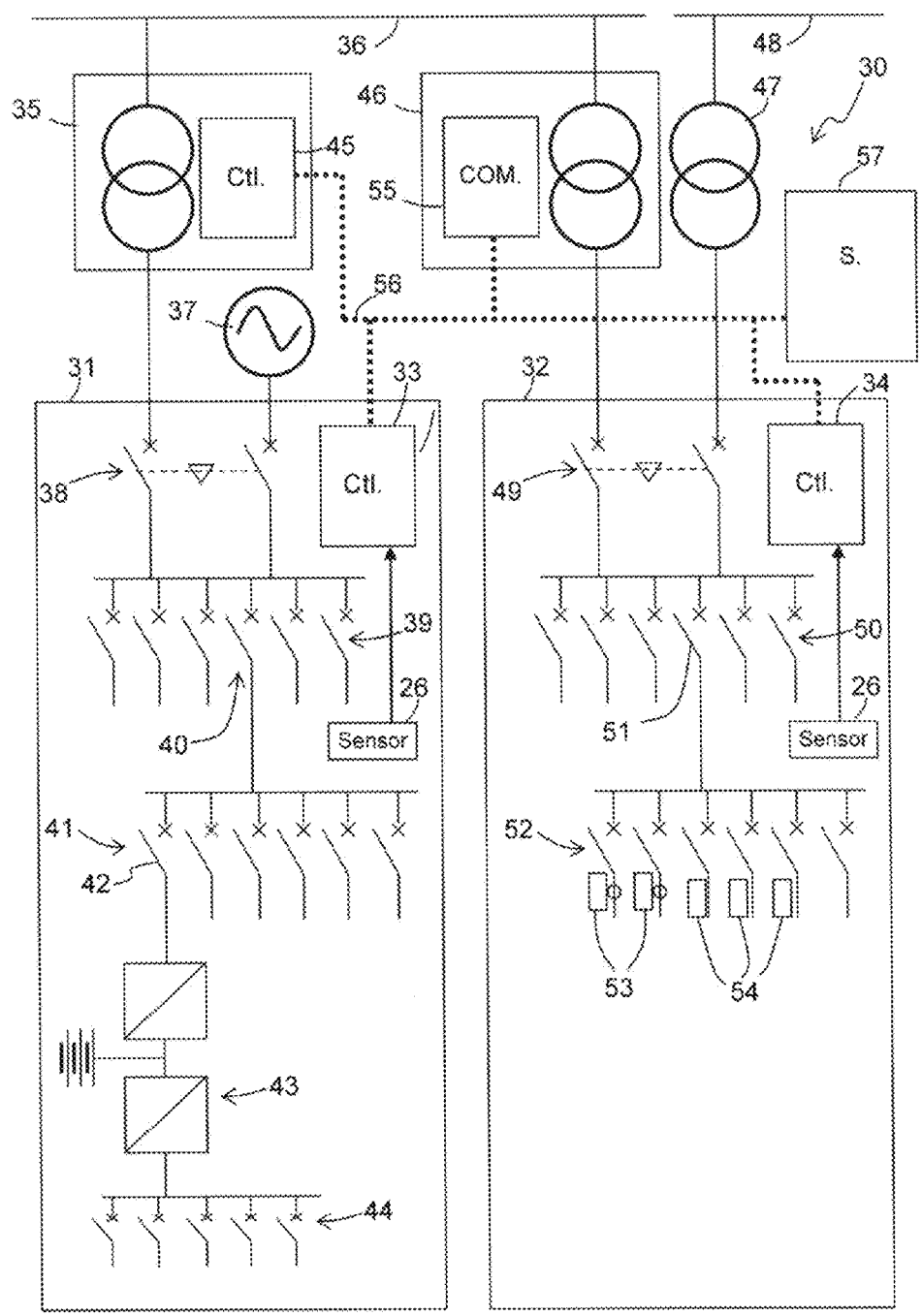
FIG. 2 represents a diagram of an electric installation comprising monitoring of ageing of electric equipment according to an embodiment of the invention.

FIG. 2 represents a diagram of an electric installation 30 comprising monitoring of ageing of electric equipment units according to an embodiment of the invention 1. In this figure, the installation comprises two electric cabinets, cubicles or panels 31, 32 each comprising an ageing monitoring device respectively 33 and 34.

Cabinet 31 is supplied on the one hand by a transformer substation 35 connected line-side to a medium-voltage electric power system 36 and on the other hand by an autonomous generator 37. These two low-voltage power supplies are input to a power supply change-over switch 38 composed of two remote-controlled and mechanically locked circuit breakers. Load-side from the changeover switch, power is supplied to a first group 39 of circuit breakers. Then a circuit breaker 40 of group 39 supplies a second group 41. A circuit breaker 42 of the second group performs load-side supply of an electric power conversion and storage device 43, and then supplies a third group 44 of circuit breakers. The transformer substation 35 can also comprise circuit breakers or disconnecting switches line-side on the medium voltage and on the low-voltage side. In each cabinet, sensors 26 measuring environmental physical quantities can be common for computing ageing of several equipment units. Ageing computation is centralized in a device 33 for the cabinet 31 or sent up to a supervisor. Each cabinet is then a climatic zone for computing ageing of the electric equipment units installed therein. Each electric equipment unit comprising a communication device sends data on operating conditions to the computation device 33. For the others, ageing computation can also be performed according to values of climatic conditions and to previously stored data.

Cabinet 32 is supplied on the one hand by a transformer substation 46 connected line-side to a medium-voltage electric power system 36 and on the other hand by a transformer 47 to a second medium-voltage electric power system 48. Load-side from the substation 46 and from the transformer 47, two low-voltage power supplies are input to a power supply change-over switch 49 composed of two remote-controlled and mechanically locked circuit breakers. Load-side from the changeover switch, power is supplied to a first group 50 of circuit breakers. Then a circuit breaker 51 of group 50 supplies a second group 52 of circuit breakers. The equipment units comprising a communication device send data on operating conditions to the control device 34. Short-circuit detectors 54 fitted on feeders enable line or load faults to be located and may also be able to provide stress data for ageing computation.

A communication device 55 located in the transformer substation 46 can also send data used for ageing computation to the control device 34.

The monitoring devices used for monitoring states, settings and characteristics, and for monitoring ageing are connected to one another by a communication network 56 and to a supervisor 57.

Figure 3:
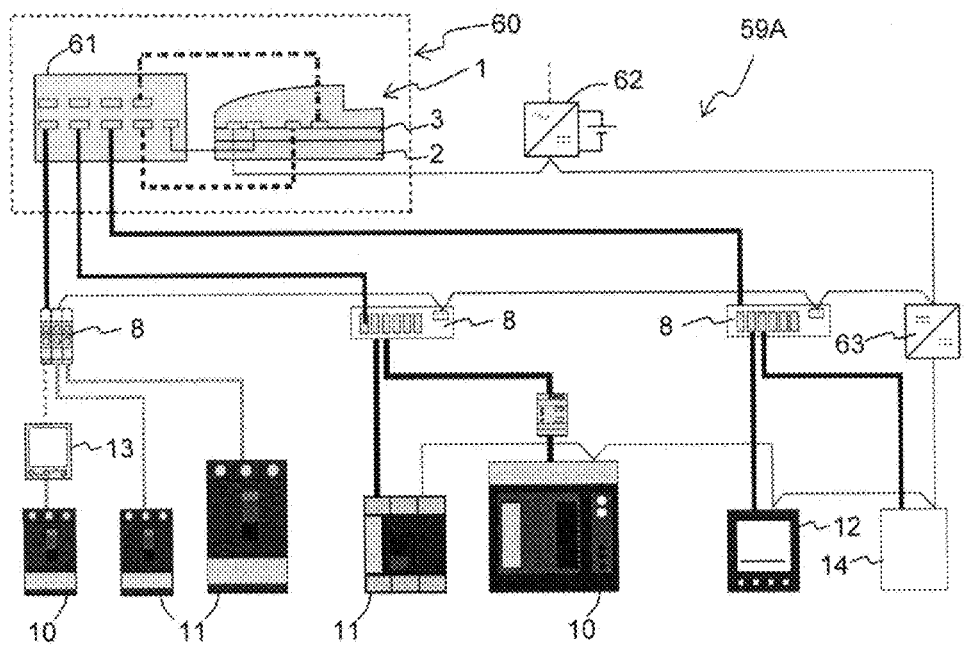
FIGS. 3 to 5 represent installations according to variants of embodiments of the invention.

FIG. 3 shows another diagram of a part of an installation 59 with a device for monitoring ageing of electric equipment units having an ageing computation processing enclosure 60 comprising a processing module 1 and a management module 61 of the communication circuits and of the inputs-outputs of different sensors. The circuit 61 is connected to communication concentrators 8 receiving data from the electric equipment units 10 to 14. The concentrators and communication circuits of the equipment units are for example supplied by the power supply circuits comprising converters 62 and 63 and also lines 64 and 65.

Figure 4:
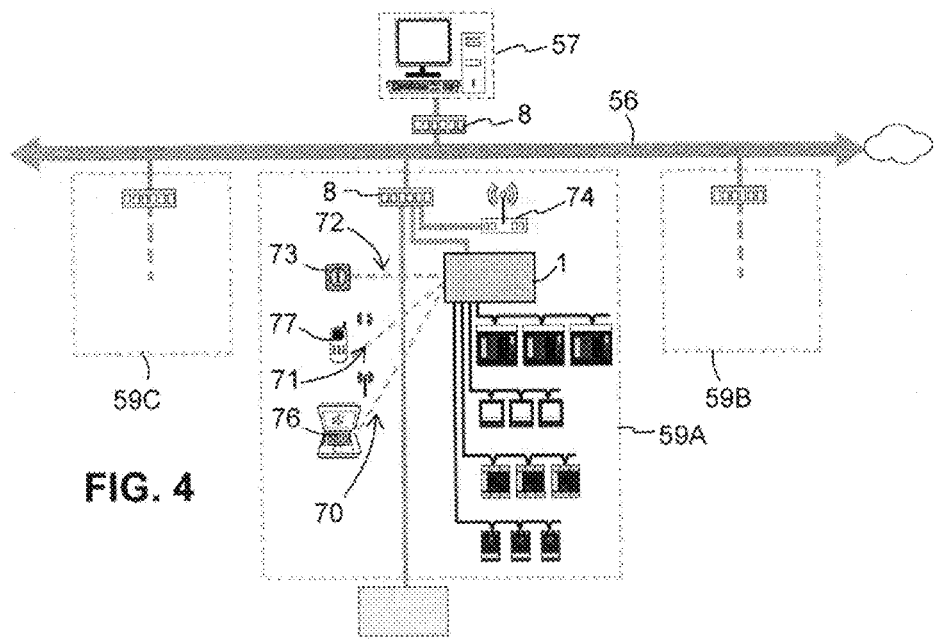
Figure 5:
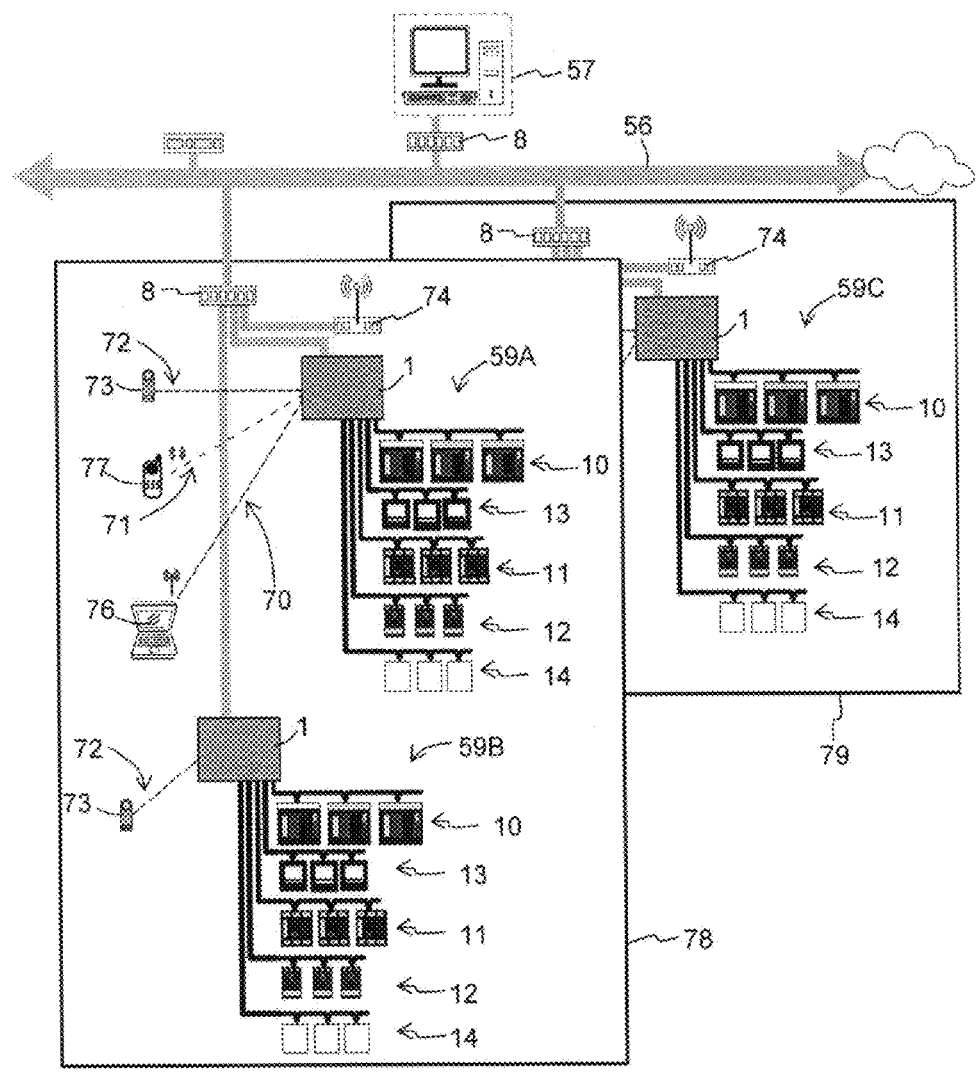

FIGS. 4 and 5 represent installations according to alternative embodiments of the invention. In FIG. 4, parts of installation 59A, 59B, 59C are connected to a communication network 56 connected to a supervisor 57. Electric equipment ageing monitoring is thus global and can be supervised by a central or remote operator. To ensure the safety and ruggedness of supervision of electric equipment ageing, computation can be performed in each ageing monitoring device. Furthermore, the diagram, setting and ageing computation data are preferably exchanged, compared and consolidated in each storage module of the monitoring devices.

The part of installation 59A comprises a wireless communication link 70, a cell phone communication link 71, and a radio communication link 72 to communicate with the ageing monitoring processing module 60. The link 72 is for example used by an enclosure 73 commanding opening or closing of an electric equipment unit such as a remote-controlled circuit breaker, a contactor, or a switching circuit breaker. Links 70 and 71 are for example used by a local operator to be informed on the state of the installation, the setting data and/or the electric equipment ageing computation data and to modify said data. A wireless communication module 74 is connected to a concentrator 8 to communicate for example with the supervisor or with other parts of the installation. Indication of ageing of electric equipment can thus also be performed on portable computers 76, wireless link tablets 70 or mobile phones 77 or a tablet via a cell phone network 71.

In FIG. 5, parts of installation 59A and 59B are for example located in the same equipment room. Certain links 70, 71 and modules 74 can thus be combined in the same equipment room 78. The links 72 with the remote control enclosures are associated with each processing module 1. In another equipment room 79, another part of an installation 59C is connected to the supervisor and to parts 59A, 59B via communication network 56.

Figure 6:
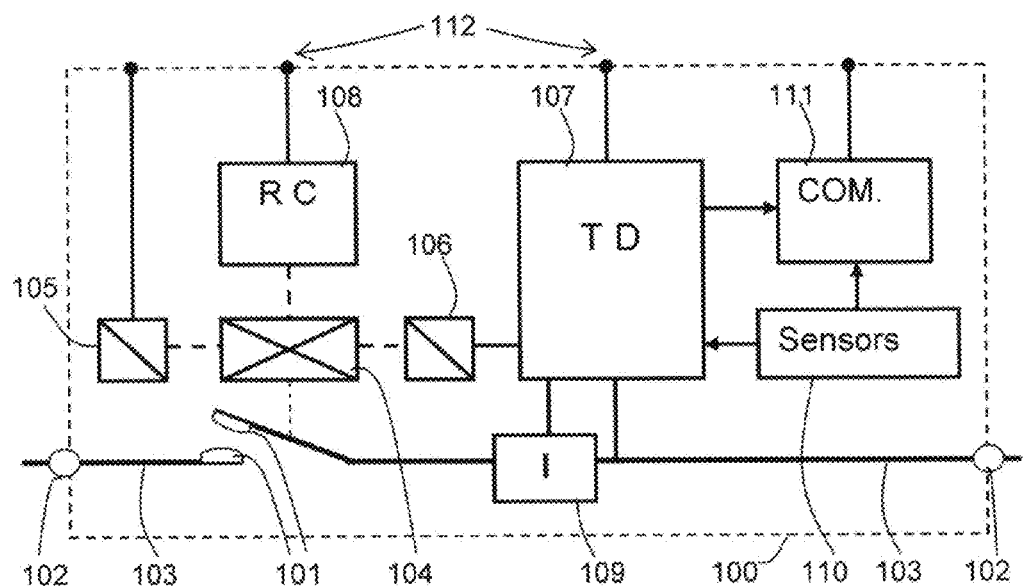
FIG. 6 represents a diagram of an electric equipment unit designed to be used with a device for monitoring ageing according to an embodiment of the invention.

FIG. 6 shows a diagram of an electric equipment unit such as a circuit breaker 100 designed to be used with an ageing monitoring device according to an embodiment of the invention. The circuit breaker comprises power contacts 101 connected to connection terminals 102 by power conductors 103. The contacts 101 are actuated by a mechanism 104 able to be controlled manually or by the control devices. In the circuit breaker of FIG. 6, the mechanism 104 is controlled by an actuator 105 such as an overvoltage and/or undervoltage release coil, by a trip relay 106 associated with a trip device 107, or by a remote-control device 108 able to open or close the contacts 101. The electronic trip device 107 receives signals representative of currents flowing in the conductors 103 and measured by the current sensors 109. Other sensors 110 are connected to the trip device 107 to provide information such as the local temperature. The circuit breaker also comprises a communication module 111 connected to the trip device and/or to sensors to provide data for performing ageing computation to the module 1. Terminals 112 enable connection of certain elements of the circuit breaker.

Figure 7:
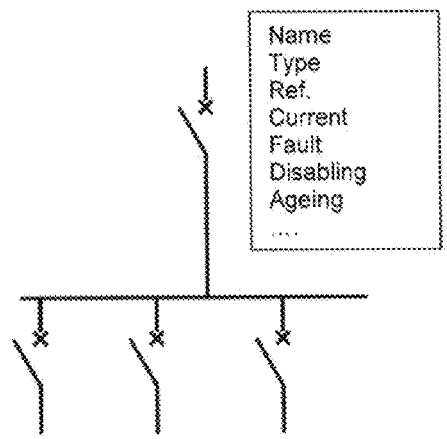
FIG. 7 represents a diagram of presentation of data of electric equipment units showing ageing data.

FIG. 7 represents a presentation diagram of the electric equipment data showing ageing data. This type of diagram can appear on monitoring and diagnostic tools 57, 76, 77.

Figure 8:
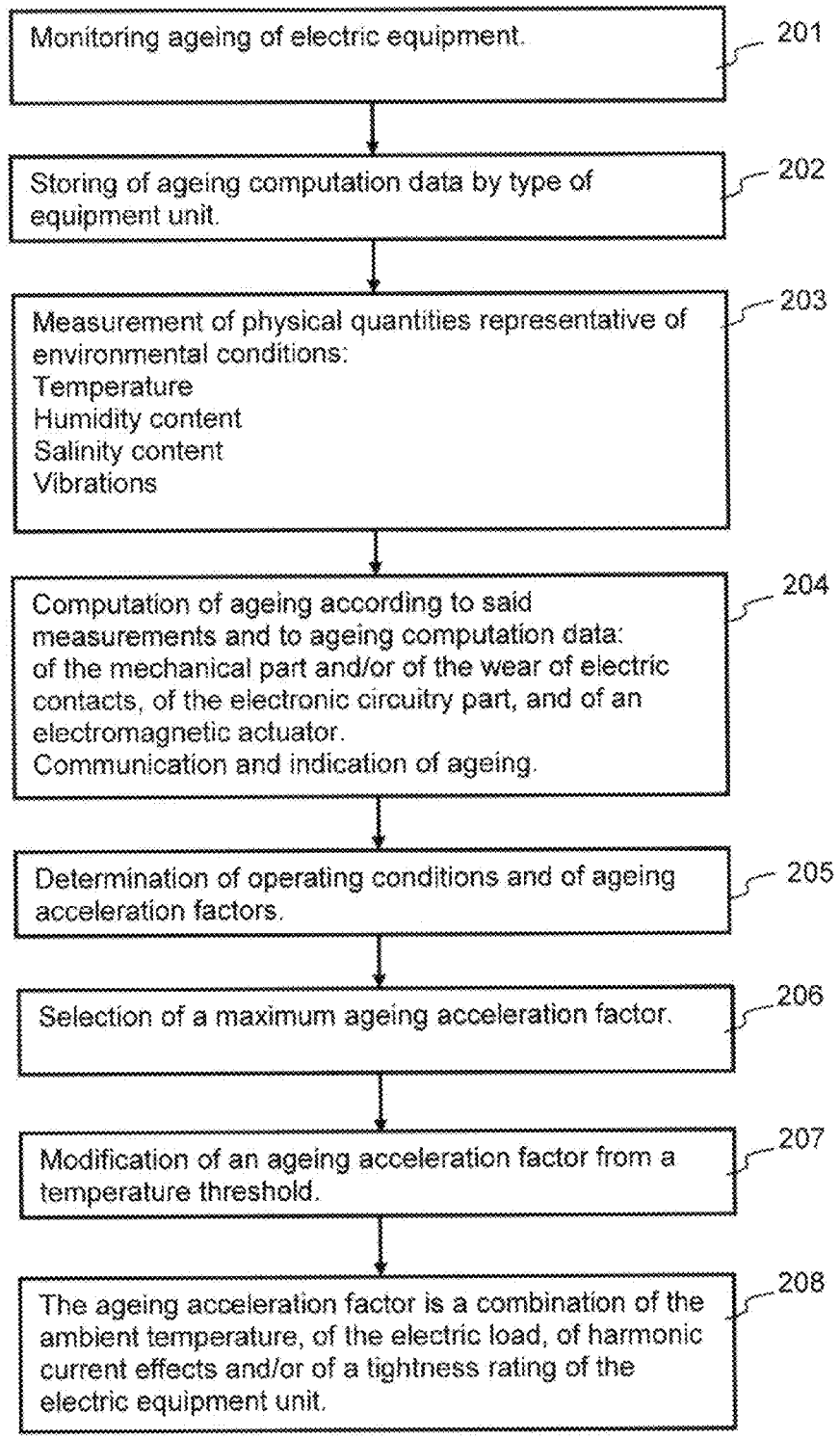
FIG. 8 represents a flowchart of a method for monitoring ageing of electric equipment units according to an embodiment of the invention.

FIG. 8 represents a flowchart of a method for monitoring ageing of electric equipment according to an embodiment of the invention.

Step 201 initializes monitoring of ageing of the electric equipment. It in particular stores the characteristics of each type or reference of electric equipment able to be used in the installation. Step 202 performs storage of ageing computation data by equipment type. The diagram is entered in single-line form defining the line-side and load-side connection points and the references of each equipment unit and settings. The diagram can be entered by means of graphic tools or imported from other software.

A step 203 performs measurement and recording of physical quantities representative of environmental conditions. Step 203 in particular comprises:
 temperature measurement and storage by a sensor close to said electric equipment units,
 measurement and storage of the humidity content,
 measurement and storage of the salinity content, and/or
 measurement and storage of amplitude and frequency of vibrations.

A step 204 performs computation of ageing according to said measurements and to the stored ageing computation data. In this step, ageing computation comprises:
 computation of ageing of the mechanical part and/or of the wear of electric contacts of said equipment unit,
 computation of ageing of the electronic part of said equipment unit, and/or
 computation of ageing of an electromagnetic actuator of said electric equipment unit.

At the end of computation, communication and/or indication of data representative of results of electric equipment ageing computation is performed.

A step 205 determines operating conditions in particular by performing:
 counting of the operations of an electric equipment unit,
 measurement of the conditions of the operations of the electric equipment unit, and
 recording of data representative of operations associated with broken current values.

Step 205 also performs determination or computation of ageing acceleration factors. A step 206 selects a maximum ageing acceleration factor from several ageing acceleration factors. Step 206 enables a certain independence of the ageing acceleration factors to be taken into account. It is also possible to weight several acceleration factors in a common factor.

In a step 207, the method modifies a value of the ageing acceleration factor due to temperature from a temperature threshold. For example, above 85° C., an electronic circuit can have a much higher ageing acceleration factor.

A step 208 assigns a combination of ageing acceleration factors to the ageing acceleration factor due to temperature, such as the ambient temperature, the type of electric load, the effects of harmonic currents and/or the tightness rating (IP) of said electric equipment unit.

In the installations described in the foregoing, the links between the equipment units are described with a hard-wired network and concentrators. These hard-wired links are preferably achieved with the "MODBUS" industrial communication standard. Other standards can however be used. The links can also be wireless links of types well known under the names of "WI-FI" or "ZigBee".

The invention claimed is:

1. A monitoring method for monitoring ageing of at least one electric equipment unit, the monitoring method comprising:
   entering and storing ageing computation data by type of equipment,
   measuring physical quantities representative of environmental conditions of the electric equipment unit, the measuring of the physical quantities including measuring humidity content with a humidity sensor and measuring salinity content with a salinity sensor;
   computing, by processing circuitry, ageing according to said measured physical quantities including the humidity content and the salinity content, and according to the stored ageing computation data; and
   generating, by the processing circuitry, electric equipment ageing data that indicates the ageing of the electric equipment unit.

2. The monitoring method according to claim 1, further comprising:
   counting operations of the electric equipment unit;
   measuring conditions of the operations of the electric equipment unit; and
   recording data representative of operations associated with broken current values.

3. The monitoring method according to claim 1, wherein the measuring of physical quantities representative of environmental conditions comprises:
   temperature measuring and storing by a sensor close to said electric equipment unit,
   storing the humidity content,
   storing the salinity content, and/or
   measuring and storing amplitude and frequency of vibrations.

4. The monitoring method according to claim 1, wherein the computing of ageing comprises:
   computing ageing of a mechanical part and/or of wear of electric contacts of said equipment unit,
   computing ageing of an electronic part of said equipment unit, and/or
   computing ageing of an electromagnetic actuator of said electric equipment unit.

5. The monitoring method according to claim 1, further comprising determining ageing acceleration factors.

6. The monitoring method according to claim 5, further comprising selecting a maximum ageing acceleration factor from several ageing acceleration factors.

7. The monitoring method according to claim 5, further comprising modifying a value of the ageing acceleration factor due to temperature from a temperature threshold.

8. The monitoring method according to claim 1, further comprising combining an ageing acceleration factor due to temperature with ageing acceleration factors representative of an ambient temperature, of an electric load, of harmonic current effects and/or of a tightness rating of said electric equipment unit.

9. A device for monitoring ageing of at least one electric equipment unit, the device comprising:
   processing circuitry designed to be connected to the at least one electric equipment unit, and configured to
      enter and store ageing computation data by type of equipment,
      measure physical quantities representative of environmental conditions of the electric equipment unit, including measuring of humidity content with a humidity sensor and measuring of salinity content with a salinity sensor,
      compute ageing according to said measured physical quantities including the humidity content and the salinity content, and according to the stored ageing computation data, and
      generate electric equipment ageing data that indicates the ageing of the electric equipment unit.

10. The monitoring device according to claim 9, wherein said processing circuitry is further configured to
   store characteristics for computing ageing of electric equipment units,
   measure inputs designed to be connected to measurement sensors of environmental physical quantities, and
   indicate ageing of the electric equipment units.

11. The monitoring device according to claim 9, further comprising measurement sensors to measure environmental physical quantities, the measurement sensors being connected to said processing circuitry.

12. The monitoring device according to claim 11, wherein the measurement sensors that measure the environmental physical quantities comprise:
   a temperature sensor situated in a space close to said electric equipment unit,
   the humidity sensor,
   the salinity sensor, and/or
   a vibration amplitude and frequency sensor.

13. An electric installation that monitors ageing of at least one electric equipment unit, the electric installation comprising:
   communication means for connecting to the electric equipment unit;
   means for entering and storing ageing computation data by type of equipment;
   means for measuring physical quantities representative of environmental conditions of the electric equipment unit, the means for measuring including measuring humidity content and measuring salinity content;
   means for computing ageing according to said measured physical quantities including the humidity content and the salinity content, and according to the stored ageing computation data; and
   means for generating electric equipment ageing data that indicates the ageing of the electric equipment unit.

14. The electric installation according to claim 13, further comprising a plurality of electric equipment units connected by the communication means to the means for computing.

* * * * *